United States Patent [19]

Milam et al.

[11] 4,089,909

[45] May 16, 1978

[54] SEPARATION OF DICHLOROBENZENE ISOMERS

[75] Inventors: Joseph E. Milam; Warren E. Dean; Robert K. Gerdes, all of New Martinsville, W. Va.

[73] Assignee: PPG Industries, Inc., Pittsburgh, Pa.

[21] Appl. No.: 725,221

[22] Filed: Sep. 22, 1976

[51] Int. Cl.$^2$ ............................................. C07C 25/10
[52] U.S. Cl. .................................................. 260/650 R
[58] Field of Search ..................................... 260/650 R

[56] References Cited

U.S. PATENT DOCUMENTS

| 2,123,857 | 7/1938 | Wieaut et al. | 260/650 R |
| 2,174,289 | 9/1939 | Levine et al. | 260/650 R |
| 3,170,961 | 2/1965 | Britton et al. | 260/650 R |

Primary Examiner—C. Davis
Attorney, Agent, or Firm—Edward J. Whitfield; Roger S. Benjamin

[57] ABSTRACT

Metadichlorobenzene is removed from mixed dichlorobenzene isomers by a liquid phase Friedel-Crafts catalyst assisted chlorination in the absence of benzene or monochlorobenzene.

5 Claims, No Drawings

SEPARATION OF DICHLOROBENZENE ISOMERS

BACKGROUND OF THE INVENTION

Mixed ortho-, meta- and para- isomers of dichlorobenzene result from the nuclear chlorination of benzene or monochlorobenzene by either liquid or vapor phase processed. In liquid phase Friedel-Crafts catalyzed nuclear chlorination processes for the synthesis of dichlorobenzene from benzene or monochlorobenzene, the meta- isomer is typically formed at concentrations of less than 2.0 weight percent of the total dichlorobenzene content. The ortho- and para- isomers produced in the liquid phase process constitute the balance of the dichlorobenzenes and are generally present in a para- to ortho- weight ratio of between 3.5:1 to 1.4:1. Recycle of meta-rich dichlorobenzene isomer mixtures into the reaction zone with benzene and monochlorobenzene feedstock results in a gradual buildup of the meta- isomer in the reaction product.

Paradichlorobenzene and orthodichlorobenzene may be separated by known distillation and crystallization techniques, however the presence of meta- isomer increases the difficulty of such separations. For many purposes, dichlorobenzene products free of metadichlorobenzene are desirable. It is especially difficult to separate metadichlorobenzene from paradichlorobenzene because of the proximity of boiling points. In addition, enough of both ortho- and meta- isomer accompany the paradichlorobenzene fraction to allow their gradual buildup to significant levels when purification of paradichlorobenzene by crystallization is practiced. This buildup results in accumulation of a waste liquor of mixed dichlorobenzene isomers having low economic value.

U.S. Pat. No. 3,170,961 describes the removal of metachlorobenzene and orthodichlorobenzene from paradichlorobenzene by selective bromination. Orthodichlorobenzene is thereafter recovered by debromination.

To conveniently separate ortho- and para- isomers of dichlorobenzene by thermal fractionation and crystallization techniques, it is desirable that a process be found to significantly reduce the meta- isomer content of the dichlorobenzene mixture.

THE INVENTION

This invention deals with removing metadichlorobenzene from metarich dichlorobenzene isomer mixtures. More particularly, this invention involves separating paradichlorobenzene and orthodichlorobenzene from metadichlorobenzene. In addition, this invention concerns an improved process for preparing and purifying paradichlorobenzene and orthodichlorobenzene wherein additional quantities of paradichlorobenzene and/or orthodichlorobenzene are recovered from mixed dichlorobenzene isomer waste streams containing metadichlorobenzene.

Particularly well suited to the process of the invention is the recovery of paradichlorobenzene and orthodichlorobenzene from waste mother liquor produced in a paradichlorobenzene purification crystallization step.

It is a discovery of this invention that special metarich chlorobenzene mixtures may be converted to metalean mixtures by selective chlorination of metadichlorobenzene. It is a discovery of this invention that metachlorobenzene in a substantially dichlorobenzene mixture chlorinates at approximately three to four times the rate of either orthodichlorobenzene or paradichlorobenzene in a liquid phase Friedel-Crafts catalyzed chlorination reaction. It is also a discovery of this invention that the preferential chlorination of meta- dichlorobenzene takes place only in the relative absence of compounds which chlorinate more readily than dichlorobenzenes, especially benzene or monochlorobenzene.

DETAILED DESCRIPTION OF THE INVENTION

Mixed dichlorobenzene isomers are produced by chlorination of benzene or monochlorobenzene by conventional liquid or vapor phase processes. Particularly convenient is the preparation of dichlorobenzenes by the liquid phase nuclear chlorination of benzene or monochlorobenzene using elemental chlorine in the presence of Friedel-Crafts catalyst. The chlorine substitution products of the liquid phase reaction cover a spectrum of nuclear substituted benzene compounds in various degrees of chlorination. For example, a liquid phase chlorination process having a maximum yield of dichlorobenzenes will concurrently produce tri-, and higher chlorobenzenes as well an include a residual portion of unreacted starting materials. Where dichlorobenzenes are desired, the production of tri- and higher polychlorobenzene production is desirably minimized as wasteful of chlorine reactant by keeping the degree of chlorine substitution of the benzene molecule at less than the theoretical value of two required for formation of dichlorobenzenes, specifically, between 1.7 and 1.9. Consequently, a moderate proportion (usually between 5 and 30 weight percent) of the reaction product is unreacted feed or monochlorobenzene. If meta- dichlorobenzene is recycled into the reaction zone (for example, with fresh feedstock), it does not exhibit a preferential chlorination with respect to other dichlorobenzene isomers present but for the most part accumulates because the chlorination preferentially proceeds predominantly with respect to the more reactive benzene or chlorobenzene feed components. Preliminary separation of the chlorination reaction product may be conveniently done by thermal fractionation to give separate fractions such as (1) unreacted starting materials; (2) a dichlorobenzene mixture; and (3) tri- and higher chlorobenzenes.

As used herein the phrase "substantially dichlorobenzene mixture" refers to a metadichlorobenzene-rich mixture of dichlorobenzene isomers containing less than 5 weight percent and preferably less than 3 weight percent of benzene, monochlorobenzene or other compounds more easily chlorinated by liquid phase Friedel-Crafts catalyzed chlorination than dichlorobenzenes with the balance of the mixture being dichlorobenzenes. A metadichlorobenzene-rich mixture refers to a mixture wherein metadichlorobenzene is present at a level of at least 10 weight percent and preferably 20 weight percent of the total dichlorobenzene content of the mixture. The "substantially dichlorobenzene mixture" (which is meta-rich) most often results from waste stream incident to purification of the dichlorobenzene mixture fraction separated from the product stream. Dichlorobenzene mixtures containing more than the above-stated limit of readily chlorinated compounds (e.g., benzene, monochlorobenzene) are not recommended for use in the process of this invention because they interfere with the selective chlorination of metadichlorobenzene. The presence of tri- and higher polychlorobenzenes in the substantially dichlorobenzene mixture is not detrimental since these compounds are generally less receptive to further chlorination than dichlorobenzenes. However, it is usually desirable to exclude all but dichlorobenzene isomers from the substantially dichlorobenzene mixture to encourage ease of operation and avoid unnecessary dilution of the product stream.

The substantially dichlorobenzene mixture contains para-, ortho- and some meta- isomers and may be thermally fractionated to separate the major (over 90 weight percent) portion of orthodichlorobenzene from the lower boiling para- and meta- isomers. The higher boiling orthodichlorobenzene fraction may be removed from a thermal fractionation column as bottoms. The paradichlorobenzene fraction (containing minor proportions of each of the meta- and ortho- isomers) removed as overhead from a thermal fractionation column may initially be purified by a series of crystallizations to remove as crystals a major portion of paradichlorobenzene having a reduced proportion of other dichlorobenzene isomers. However, a waste mother liquor from the crystallization process having increased meta- isomer content is formed and makes further separation of isomers impractical. This mixed isomer waste stream typically containing high proportions of meta- isomer together with ortho- isomer and para- isomer may then be further treated according to the process of this invention.

The process of this invention is particularly applicable to a metarich feedstock containing at least 20 weight percent each of metadichlorobenzene, orthodichlorobenzene and paradichlorobenzene. A feedstock of this composition is typically that of the waste mother liquor of a paradichlorobenzene crystallization purification.

Reaction conditions for removal of metadichlorobenzene from a predominantly dichlorobenzene mixture are the same as those employed in the synthesis of dichlorobenzenes from benzene or monochlorobenzene feedstock using elemental chlorine in a liquid phase Friedel-Crafts catalyst assisted chlorination. The reaction media is most conveniently the liquid dichlorobenzene mixture itself although other inert liquid media may be used (e.g., tetrachloroethane). The reaction temperature should be between 20° to 180° C. and preferably between 40° to 70° C. Typical reaction time is between 15 minutes and 4 hours. The catalyst for promotion of the conversion of metadichlorobenzene to trichlorobenzene may be any Friedel-Crafts catalyst having utility for nuclear chlorination reactions in liquid phase such as ferric chloride, tin chloride or aluminum chloride, but ferric chloride is especially preferred. Catalyst concentration is not critical and is typically less than 5 weight percent of the feedstock, with a catalyst concentration of 0.1 to 4 weight percent being preferred.

Metadichlorobenzene chlorinates at several times the rate of ortho- and para- dichlorobenzene. The removal of meta- isomer from the predominantly dichlorobenzene mixture by chlorination to 1,2,4-trichlorobenzene may be gauged by the degree of chlorination of the reaction mixture. By "degree of chlorination" is meant the calculated average number of chlorine atoms per gram atomic weight of benzene. The initial degree of chlorination for the predominantly dichlorobenzene mixture is about 2.0. The degree of chlorination necessary to remove the major portion of metadichlorobenzene is generally between 2.1 to 2.8 and more desirably between 2.2 and 2.7. The extent to which chlorination should be carried out will depend on the objectives of the operation. The greater the extent of meta- isomer removal desired, the greater is the concurrent although proportionately smaller conversion of para- and ortho- isomers to trichlorobenzenes. If need exists for tri- or higher polybenzene products, then a high degree of chlorination may be employed. Alternately, if as much as possible of the ortho- and para- isomer values in the substantially dichlorobenzene mixture are to be preserved, then meta- isomer is reacted to the least extent that will permit convenient separation of ortho- and para- isomers by conventional means such as thermal fractionation and crystallization. Generally, it is desirable to conduct the chlorination of the predominantly dichlorobenzene mixture until the meta- isomer content is reduced to below 10 and preferably below 5 weight percent based on the weight of dichlorobenzenes in the mixture. If desired, the process of chlorinating a substantially dichlorobenzene mixture may be conducted repeatedly, interspersed with conventional distillative and crystallization processing for separation and purification of ortho- and para- isomers and by-product trichlorobenzenes.

It is desirable to conduct the process in the absence of water and oxygen since these agents tend to increase corrosion and promote formation of unwanted by-products.

The reactor for the performance of the process of this invention may be of any conventional design that provides an inlet, an outlet and means for controlling the reactor temperature (e.g., heat exchange coils). The construction materials should be those which are resistant to the feedstock reaction products and chlorination atmosphere, for example, glass or nickel. The catalyst may be employed as a fluidized bed or a fixed bed or alternately the catalyst be continuously supplied with the feedstock and withdrawn with the reaction product.

The following example illustrates the practice of this invention.

EXAMPLE

A feedstock of waste mother liquor from a paradichlorobenzene crystallization was employed in the following experiments:

| Waste Mother Liquor Composition | |
|---|---|
| | Weight % |
| Benzene | 0.08 |
| Monochlorobenzene | 1.58 |
| Paradichlorobenzene | 35.81 |
| Metadichlorobenzene | 35.77 |
| Orthodichlorobenzene | 26.76 |

Approximately 500 ml. of the feedstock was placed in a blackened 1000 ml. round-bottom three-neck flask fitted with inlet and outlet tubes, stirrer, condenser, and thermometer. The flask was immersed in a thermally regulated water bath for temperature control. Elemental chlorine feed was continuously supplied at a rate in excess of stoichiometric requirements for conversion of dichlorobenzenes to trichlorobenzenes to determine the chlorination rate.

The experiments were conducted at 43°, 66° and 100° C. The catalyst used for all experiments was anhydrous $FeCl_3$ at 0.50 percent by weight on the basis of organic compounds charged to the flask. The results are set out in Table I, II, III, and IV below:

TABLE I

| | Chlorination at 100° C. | | | | | | | |
|---|---|---|---|---|---|---|---|---|
| Running Time, Minutes | 0 | 35 | 60 | 90 | 120 | 155 | 180 | 210 |
| Composition, Wt. % | | | | | | | | |
| Benzene | 0.08 | 0.06 | 0.04 | 0.05 | 0.03 | — | — | — |
| MCB | 1.58 | 0.16 | 0.02 | 0.01 | 0.01 | — | — | — |
| p-DCB | 35.81 | 33.57 | 31.90 | 26.35 | 16.45 | 12.48 | 9.70 | 5.68 |
| m-DCB | 35.77 | 19.85 | 6.84 | 2.57 | 0.01 | 0.01 | — | — |
| o-DCB | 26.76 | 22.34 | 18.92 | 12.51 | 6.26 | 1.48 | 0.35 | 0.01 |
| 1,3,5 Tri- | — | — | 0.03 | 0.01 | 0.01 | 0.01 | 0.01 | — |
| 1,2,4 Tri- | — | 18.64 | 32.61 | 44.01 | 54.42 | 49.44 | 45.76 | 36.88 |
| 1,2,3 Tri- | — | 4.64 | 8.28 | 9.29 | 9.13 | 6.80 | 4.77 | 2.30 |
| Heavies | — | 0.74 | 1.36 | 5.80 | 13.68 | 29.78 | 39.41 | 55.13 |

TABLE II

| | Chlorination at 66° C. | | | | | |
|---|---|---|---|---|---|---|
| Running Time, Minutes | 0 | 30 | 60 | 90 | 120 | 150 |
| Composition, Wt. % | | | | | | |
| Benzene | 0.08 | 0.07 | 0.04 | 0.05 | — | — |
| MCB | 1.56 | 0.25 | — | — | — | — |
| p-DCB | 35.81 | 33.54 | 30.13 | 24.12 | 21.32 | 9.06 |
| m-DCB | 35.77 | 22.98 | 10.04 | 2.40 | — | — |
| o-DCB | 26.76 | 23.87 | 17.88 | 12.32 | 5.38 | 0.99 |
| 1,3,5 Tri- | — | — | — | — | — | — |
| 1,2,4 Tri- | — | 16.08 | 32.54 | 44.59 | 52.33 | 55.26 |
| 1,2,3 Tri- | — | 3.03 | 7.88 | 11.20 | 8.79 | 6.07 |
| Heavies | — | 0.16 | 1.50 | 5.31 | 12.17 | 28.62 |

TABLE III

| | Chlorination at 43° C. | | | | | |
|---|---|---|---|---|---|---|
| Running Time, Minutes | 30 | 60 | 90 | 120 | 150 | 180 |
| Composition, Wt. % | | | | | | |
| Benzene | 0.05 | 0.05 | 0.03 | — | — | — |
| MCB | 0.16 | — | — | — | — | — |
| p-DCB | 35.50 | 30.33 | 25.32 | 21.41 | 15.33 | 10.01 |
| m-DCB | 22.03 | 8.60 | 1.30 | 0.01 | — | — |
| o-DCB | 23.21 | 17.72 | 9.94 | 3.73 | 0.79 | 0.08 |
| 1,3,5 Tri- | — | — | — | — | — | — |
| 1,2,4 Tri- | 18.57 | 33.88 | 47.93 | 53.12 | 53.78 | 48.29 |
| 1,2,3 Tri- | 0.27 | 8.03 | 9.93 | 8.71 | 6.04 | 3.81 |
| Heavies* | 0.20 | 1.39 | 5.56 | 13.03 | 24.07 | 37.81 |

*"Heavies" refers to combined analysis for tetrachlorobenzenes and pentachlorobenzenes.

TABLE IV

| | CONVERSIONS VS. TIME | | | | | | | |
|---|---|---|---|---|---|---|---|---|
| Running Time, Minutes | 30 | 35 | 60 | 90 | 120 | 150 | 155 | 180 |
| % Meta Converted | | | | | | | | |
| 43° C. | 35.79 | — | 73.52 | 95.81 | 99.97 | — | — | — |
| 66° C. | 33.01 | — | 69.28 | 92.31 | 100.00 | — | — | — |
| 100° C. | — | 53.84 | 79.06 | 91.85 | 99.97 | — | — | — |
| % Para Converted | | | | | | | | |
| 43° C. | — | — | 9.77 | 21.19 | 30.85 | 48.56 | — | 65.13 |
| 66° C. | 2.34 | — | 7.93 | 22.81 | 29.15 | 67.87 | — | — |
| 100° C. | — | — | 6.41 | 19.94 | 43.61 | — | 57.86 | 64.97 |
| % Ortho Converted | | | | | | | | |
| 43° C. | 9.57 | — | 27.09 | 57.21 | 83.33 | 96.33 | — | 99.61 |
| 66° C. | 7.00 | — | 26.89 | 47.24 | 76.08 | 95.30 | — | — |
| 100° C. | — | 7.19 | 22.59 | 46.98 | 71.86 | — | 93.02 | 98.30 |
| "X" Value* | | | | | | | | |
| 43° C. | 2.157 | — | 2.383 | 2.623 | 2.806 | 3.004 | — | 3.203 |
| 66° c. | 2.157 | — | 2.377 | 2.595 | 2.782 | 3.121 | — | — |
| 100° C. | — | 2.221 | 2.382 | 2.575 | 2.838 | — | 3.081 | 3.221 |

*"X" Value equals gram atoms of chlorine per gram atom of benzene.

The experimental results in the above Tables show that metadichlorobenzene may be removed from a predominantly dichlorobenzene mixture by preferential chlorination.

The process of this invention may be carried out as described below.

Benzene and monochlorobenzene are introduced as liquids into a chlorination reactor. A 2 weight percent concentration of ferric chloride catalyst is mixed with the reactants. The temperature is raised to 35° C. and the reaction allowed to proceed to a degree of chlorination of 1.8.

The reaction product consisting of benzene and mixed chlorobenzenes passed to a first fractionation zone where the major portion of unreacted benzene and monochlorobenzene are removed as overhead. The first zone bottoms consisting of di- and higher chlorobenzenes is then thermally fractionated in a second zone to produce an overhead stream of mixed meta- and para-dichlorobenzenes. The bottoms portion from the second fractionation zone consisting of orthodichlorobenzene plus tri- and higher polychlorobenzenes is sent to a separate unit for further fractionation to recover purified orthodichlorobenzene. The previously segregated overhead stream of mixed meta- and para- isomers (also containing residual ortho- isomer) is crystallized to remove as crystals the purified paradichlorobenzene.

The liquid waste mother liquor of the crystallization is reacted in a reaction zone with elemental chlorine at 40° C. in the presence of 3 percent by weight of ferric chloride catalyst. The chlorination is continued until a degree of chlorination of 2.5 is obtained. This chlorinated reaction product is thermally fractionated to remove dichlorobenzenes as overhead and tri- and higher polychlorobenzenes as bottoms. Orthodichlorobenzene is then separated in another fractionation zone as bottoms and the overhead stream containing predominantly paradichlorobenzene is purified by crystallization. Waste mother liquor from this crystallization is stored for use as a substantially dichlorobenzene mixture feed for purification and removal of metadichlorobenzene according to the process of this invention.

It will be understood that various changes and modifications can be made in details of the described metadichlorobenzene removal process and ortho- and para-isomer purification method without departing from this invention, and that all such changes are intended to be included within the scope of the claims.

We claim:

1. A process for preferentially chlorinating metadichlorobenzene to form 1,2,4-trichlorobenzene and higher polychlorobenzenes in a substantially dichlorobenzene mixture comprising at least 20 weight percent each of metadichlorobenzene, orthodichlorobenzene and paradichlorobenzene by reacting said mixture with elemental chlorine in a liquid phase Friedel-Crafts catalyst assisted chlorination at a temperature between 20° and 180° C. for a time sufficient to give a reaction product having a degree of chlorination between 2.1 and 2.8.

2. The process of claim 1 wherein the substantially dichlorobenzene mixture is chlorinated to a degree of chlorination between 2.2 and 2.7.

3. The process of claim 1 wherein the substantially dichlorobenzene mixture is chlorinated at a temperature between 40° to 70° C.

4. The process of claim 1 wherein the chlorination is conducted for a time between 15 minutes and 4 hours.

5. The process of claim 1 wherein the Friedel-Crafts catalyst is ferric chloride.

* * * * *